United States Patent
Sarvazyan et al.

(10) Patent No.: US 6,595,933 B2
(45) Date of Patent: Jul. 22, 2003

(54) SELF-PALPATION DEVICE FOR EXAMINATION OF BREAST WITH 3-D POSITIONING SYSTEM

(75) Inventors: Armen P. Sarvazyan, Lambertville, NJ (US); Vladimir Egorov, Plainsboro, NJ (US)

(73) Assignee: Artann Laboratories, Lambertville, NJ (US)

(*) Notice: Subject to any disclaimer, the term of this patent is extended or adjusted under 35 U.S.C. 154(b) by 0 days.

(21) Appl. No.: 09/876,565

(22) Filed: Jun. 7, 2001

(65) Prior Publication Data

US 2001/0031934 A1 Oct. 18, 2001

Related U.S. Application Data (63) Continuation-in-part of application No. 09/819,220, filed on Mar. 28, 2001, now Pat. No. 6,468,231.
(60) Provisional application No. 60/193,985, filed on Mar. 31, 2000.

(51) Int. Cl.$^7$ ................................................ A61B 5/103
(52) U.S. Cl. ........................................ 600/587; 600/595
(58) Field of Search ................................ 600/372, 449, 600/587, 443, 595, 407, 382, 437–447; 382/128, 154; 33/511; 73/81

(56) References Cited

U.S. PATENT DOCUMENTS

| 4,250,894 A | 2/1981 | Frei et al. ............. 600/587 |
| 4,657,021 A | 4/1987 | Perry et al. ........... 600/300 |
| 4,793,354 A | 12/1988 | Wright et al. .......... 600/300 |
| 5,265,612 A | 11/1993 | Sarvazyan et al. ...... 600/471 |
| D348,618 S | 7/1994 | Leslie et al. .......... D10/64 |
| 5,524,636 A | 6/1996 | Sarvazyan et al. ...... 600/587 |
| 5,572,995 A | 11/1996 | Rohrberg .............. 600/300 |
| 5,640,325 A | 6/1997 | Banbrook et al. ....... 701/220 |
| 5,833,633 A | 11/1998 | Sarvazyan ............. 600/587 |
| 5,833,634 A | 11/1998 | Laird et al. ........... 600/587 |
| 5,860,934 A | 1/1999 | Sarvazyan ............. 600/587 |
| 5,916,180 A | 6/1999 | Cundari et al. ........ 600/587 |
| 5,989,199 A | 11/1999 | Cundari et al. ........ 600/587 |
| 6,091,981 A | 7/2000 | Cundari et al. ........ 600/407 |
| 6,162,191 A | 12/2000 | Foxlin ................ 600/595 |
| 6,179,790 B1 * | 1/2001 | Cundari et al. ........ 600/587 |
| 6,190,334 B1 | 2/2001 | Lasky et al. .......... 600/587 |
| 6,192,143 B1 | 2/2001 | Souluer ............... 382/128 |
| 6,205,401 B1 | 3/2001 | Pickhard et al. ....... 701/220 |
| 6,351,549 B1 * | 2/2002 | Souluer ............... 382/131 |
| 6,468,231 B2 * | 10/2002 | Sarvazyan et al. ...... 600/587 |

OTHER PUBLICATIONS

C.R. Gentle, "Mammobarography: a possible method of mass breast screening," J. Biomed Eng., vol. 10, pp. 124–126, 1988.

* cited by examiner

Primary Examiner—Charles A. Marmor, II
(74) Attorney, Agent, or Firm—Mathews, Collins, Shepherd & McKay, P.A.

(57) ABSTRACT

A method and device for high resolution 3-D detection of changes in mechanical and structural properties of the breast tissue that are indicative of breast cancer development. A compact hand held device comprises a pressure sensor array, a self-contained motion tracking system integrated with the pressure sensor array, and an electronic unit with a display. Mechanical imaging of the breast is achieved by pressing the sensing pad onto the breast, oscillating it over breast tissue portions with sequential returning to a reference point. Analysis of pressure response data for oscillatory deformations comprises cumulative summation of a plurality of pressure patterns after spatially shifting every pattern by a pre-calculated value in an opposite direction of pressure sensor array motion. Determining mechanical and geometrical features of the breast inner structures includes formation of a 3-D mechanical image of the breast combining results of local scanning at all breast sites.

17 Claims, 8 Drawing Sheets

SELF-PALPATION DEVICE FOR EXAMINATION OF BREAST WITH 3-D POSITIONING SYSTEM

CROSS REFERENCE TO RELATED APPLICATION

This application is a continuation-in-part of U.S. patent application Ser. No. 09/819,220 filed Mar. 28, 2001, now U.S. Pat. No. 6,468,231 which claims the benefit of U.S. Provisional Application No. 60/193,985, filed Mar. 31, 2000. The full disclosure of above-described applications is incorporated herein by reference.

This invention was made with government support under SBIR Grants No. 1 R43 CA65246-01 A1 and No. 2 R44 CA 59175-03 awarded by the National Institutes of Health, National Cancer Institute. The government has certain rights in this invention.

BACKGROUND OF THE INVENTION

1. Technical Field

The present invention relates to a method and apparatus for breast self-palpation and detecting changes of mechanical properties in the breast tissue that are indicative of breast cancer and other breast pathologies accompanied by changes in tissue viscoelasticity.

2. Description of the Prior Art

Despite the clear advantages of annual mammography screening, less than half of American women have ever had a single mammogram. Limitations and constraints in wider and effective use of mammography include: high price of devices, large equipment size and weight, insensitivity to certain cancers readily detectable by palpation, limitations imposed by the safety aspects of the use of ionizing radiation, and patient discomfort.

Palpatory self-examination, widely advised and taught to women as means of preclinical testing, contributes substantially to early cancer detection. Women themselves, who bring the problem to their physicians, first detect a significant fraction of breast cancer. The major drawbacks of manual palpation include the necessity to develop special skills to perform self-examination, subjectivity and relatively low sensitivity. Women often do not feel comfortable and confident to make a decision whether there really are changes in the breast, and whether they should bring them to the attention of their doctors.

In order to increase the sensitivity of palpation and allow data acquisition and analysis, a number of devices for mimicking breast palpation to detect tumors have been described. For example, Frei et al., U.S. Pat. No. 4,250,894, describe an instrument for breast examination that uses a plurality of spaced piezoelectric strips which are pressed into the body being examined by a pressure member which applies a given periodic or steady stress to the tissue beneath the strips. A signal processor interrogates the output voltage of each of the strips and the output is displayed to produce a display characteristic that shows the presence of an inclusion in the breast tissue being examined. U.S. Pat. No. 5,524,636, issued to one of the inventors of the present disclosure, describes a method and apparatus for imaging a portion of the body tissue comprising a support for a portion of the tissue, and a force applying member that tends to deform the tissue relative to a reference position, while at the same time a pressure pattern distribution is generated indicating areas of greater pressure. U.S. Pat. No. 5,833,634 issued to Laird et al. discloses a tissue examination device that includes a transducer element for generating a signal in response to force imposed on the transducer element in accordance with the varying properties of the underlying tissue structure and circuitry for detecting a variation in the signal as an indication of a localized area of stiffer tissue within the tissue.

A number of breast examination devices for clinical use based on computerized mechanical palpation have also been described. U.S. Pat. No. 5,860,934 issued to one of the inventors of the present disclosure, discloses a method and device that enables detecting regions of breast tissue having a modulus of elasticity different from that of surrounding glandular tissue using a pressure sensing array. Detecting of breast tumors is based on analyzing features of the stress pattern on the surface of an examined tissue that is a deviation from a stress pattern for a relatively homogeneous normal tissue. U.S. Pat. No. 6,091,981 issued to Cundari at al. describes a device that includes sensors which produce signals in response to pressure imposed on the sensors as the sensors are pressed against the breast tissue. A location or a map of detected underlying tissue structure relative to a reference point is generated and displayed. U.S. Pat. No. 6,192,143 B1 describes a computer controlled apparatus for detecting breast tumors by mechanically palpating in a full surface scan manner in order to detect small lumps or other anomalies. A palpation finger is brought into pressure contact with a sequence of small areas across the entire breast. Concurrent with the palpation scan, a scan of breast color and temperature is conducted. U.S. Pat. No. 6,190,334 B1 discloses an apparatus for automated breast palpation including an actuator having an extendable probe for contacting the tissue and an electronic control module. A signal processor receives the force and the displacement distance determinations from the electronic control module and analyzes these data to provide a visual data analysis indicating any lesion within the tissue.

There have been attempts to develop hand held self-palpation devices for sensing regions of hardening in breast tissue and thus mimicking manual palpation for detection of breast cancer. U.S. Pat. No. 5,833,633 issued to one of the inventors of the present disclosure, discloses a hand held pad comprising a pressure sensor array, data acquisition circuit, and microprocessor. Detection of nodules is achieved by analyzing the dynamic and spatial features of the pressure pattern while the probe is pressed to the breast and is periodically moved transversely to the ribs. U.S. Pat. Nos. 5,916,180 and 5,989,199 reissued to Cundari et al. describe several devices designated to assist the user in performing breast self-examination. These devices include an array of pressure sensors, electronic circuit and warning indicator. A plurality of processing tests is performed on the received signals from the pressure sensors, and different types of tissue structures are discriminated from each other based on the results of the tests.

While the above-described conventional devices may be valuable tools for breast cancer detection, the devices have certain limitations. Specifically, the conventional devices cannot be used for a regular home use in a repeatable pattern that allows for accurate serial studies. One of the reasons is absence of motion tracking system in the conventional self-palpation devices. Therefore, there is a continuing need for an improved hand held self-palpation device comprising a motion tracking system and corresponding methods for reproducible 3-D breast mapping.

Typical conventional motion tracking systems (magnetic, mechanical, optical, and acoustical) use interactions with another component of the device that is located a distance from the main part of the device being tracked. With a magnetic motion tracking system, a magnetic field transmitter is provided which is spaced from the magnetic field receiver mounted on the tracked device. With an optical or acoustical motion tracking system, light or sound sources are provided at a known location. Mechanical trackers are connected to a reference through an arm-like device. The above-described motion tracking systems do not provide a self-contained apparatus for mounting on the device to be tracked, which apparatus can track the trajectory and orientation of the device without interaction with radiation or energy from any other apparatus. Such a self-contained motion tracking system is desirable for a hand held self-palpation device.

Conventional navigation systems using accelerometers and gyroscopes or magnetometers have been used for ships, planes, missiles and spacecraft. This navigation system is a type of self-contained motion tracking system, as that term is used herein. The main problem with using accelerometer based motion tracking systems in different kinds of devices is drift. Drift arises from double integrating over time a signal that is noisy or has a bias which is sometimes compared with the signal. This problem can be solved for a particular application by taking into account the particular qualities of the described system. For example, U.S. Pat. No. 5,640,325, issued to Bandbrook et al. discloses a system, which uses silicon accelerometers and fiber optic gyroscopes for detecting the position and orientation of a towed array of acoustic sensors used for target detection. U.S. Pat. No. 6,205,401, issued to Pickhard et al., describes a navigation system for a vehicle having six-axis gyroscopes and two accelerometers in the horizontal vehicle plane. To reduce the noise and drift errors supporting signal devices, a satellite receiver is used. U.S. Pat. No. 6,162,191 issued to Foxin reveals the details of an inertial orientation tracker having automatic drift compensation for tracking the human head. The drift compensator includes a gravitational tilt sensor or an Earth's magnetic field sensor. In all the above-described patents the received position and orientation data are processed over time by different Kalman filters to reduce the error in motion tracking determinations.

It is desirable to provide a hand held self-palpation device with 3-D self-contained positioning system for a regular home breast mapping which is easy to use and would facilitate regular self-examinations conducted by women, thereby leading to improvement in early detection of breast cancer.

SUMMARY OF THE INVENTION

The self-palpation device of the present invention utilizes the same mechanical information as obtained by manual palpation conducted by a skilled physician but objectively and with higher sensitivity and accuracy. The present method and device provides detection of tissue heterogeneity and hard inclusions by measuring changes in the surface stress pattern using a pressure sensor array applied to the tissue in the oscillatory mode along with motion tracking data analysis. Calculation of pressure sensor array trajectory and orientation comprises processing data received from a self-contained motion tracking system and correcting said trajectory and orientation via suitable Kalman filter using pressure response data from said pressure sensor array. An analysis of pressure response data for oscillatory deformations comprises cumulative summation of a plurality of pressure response frames after spatially shifting every frame by a pre-calculated amount taking into account direction of the pressure sensor array displacement. The present device and method determines mechanical and geometrical features of the breast inner structures by formation of a 3-D mechanical image of the breast combining results of local scanning at all breast sites using a calculated position and orientation data from the pressure sensor array.

The method and device in accordance with the teachings of the present invention enable the user to detect changes in the breast tissue that could be indicative of cancer development. The device of the present invention comprises a plurality of pressure sensors arranged in a two-dimensional pressure sensor array, a self-contained motion tracking system integrated with the pressure sensor array, and an electronic unit for providing acquisition of signals from the pressure sensor array and motion tracking system for processing, real time displaying, and storing received data. Detection of nodules is achieved by analyzing the dynamic and spatial features of the measured signals obtained by pressing the probe to the breast and oscillating it over the area under investigation.

The present invention provides a hand held self-palpation device for home breast investigation that generates reproducible 3-D images of the inner mechanical structure of the breast. It will become hereinafter apparent, the nature of the invention may be more clearly understood by referencing to the following detailed description of the invention, the appended claims and the several views illustrated in the drawing.

DETAILED DESCRIPTION OF THE INVENTION

Reference will now be made in greater detail to preferred embodiments of the invention, examples of which are illustrated in the accompanying drawings. Wherever possible, the same reference numerals will be used throughout the drawings and the description to refer to the same or like parts.

Figure 1:
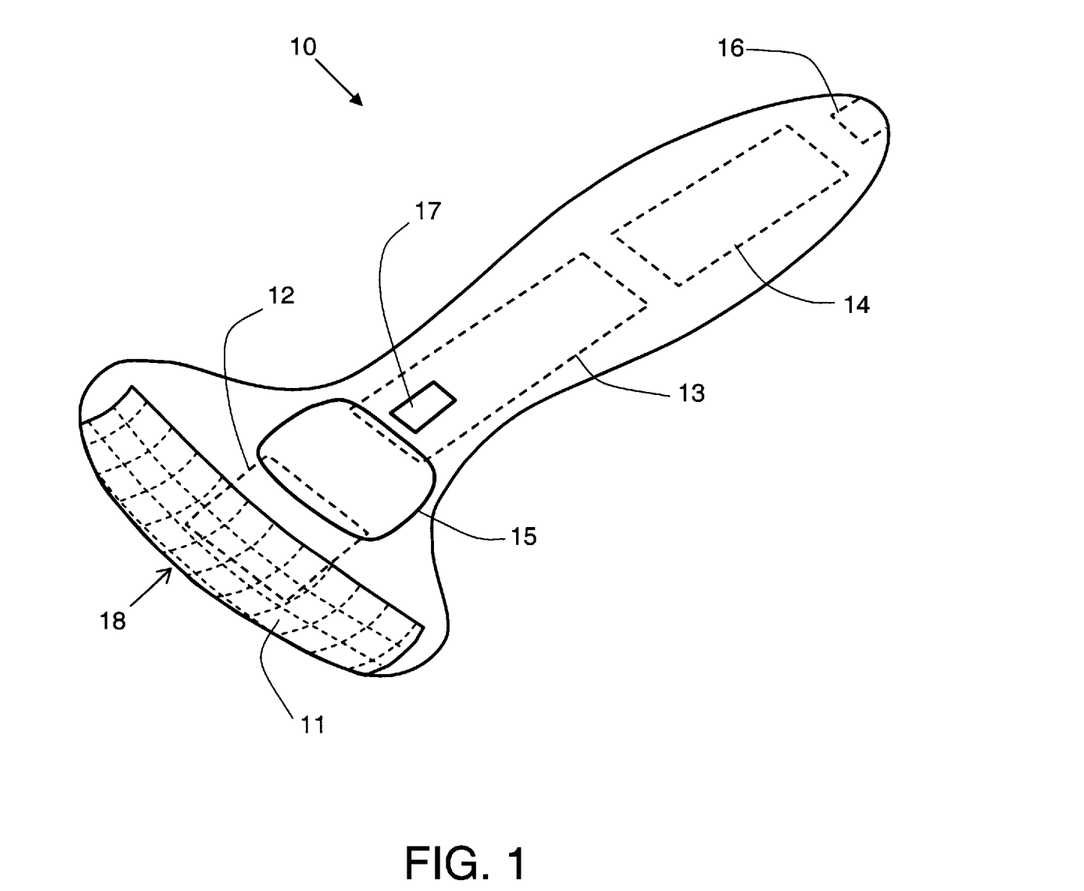
FIG. 1 is a perspective view of an embodiment of the hand held self-palpation device of the present invention including a pressure sensor array, a self-contained motion tracking system integrated with the pressure sensor array, and an electronic unit with a display.

FIG. 1 shows a hand held self-palpation device 10 for mechanical imaging of the breast in accordance with the present invention. Device 10 comprises a two-dimensional pressure sensor array 11, a self-contained motion tracking system 12, electronic unit 13, power supply 14, display 15, computer connector 16, and control wheel 17. Pressure sensor array 11 generates signals in response to pressure imposed on a pressure-sensing surface 18 as it is pressed against and moved over the breast. Motion tracking system 12 generates signals in response to motion of device 10.

Figure 2:
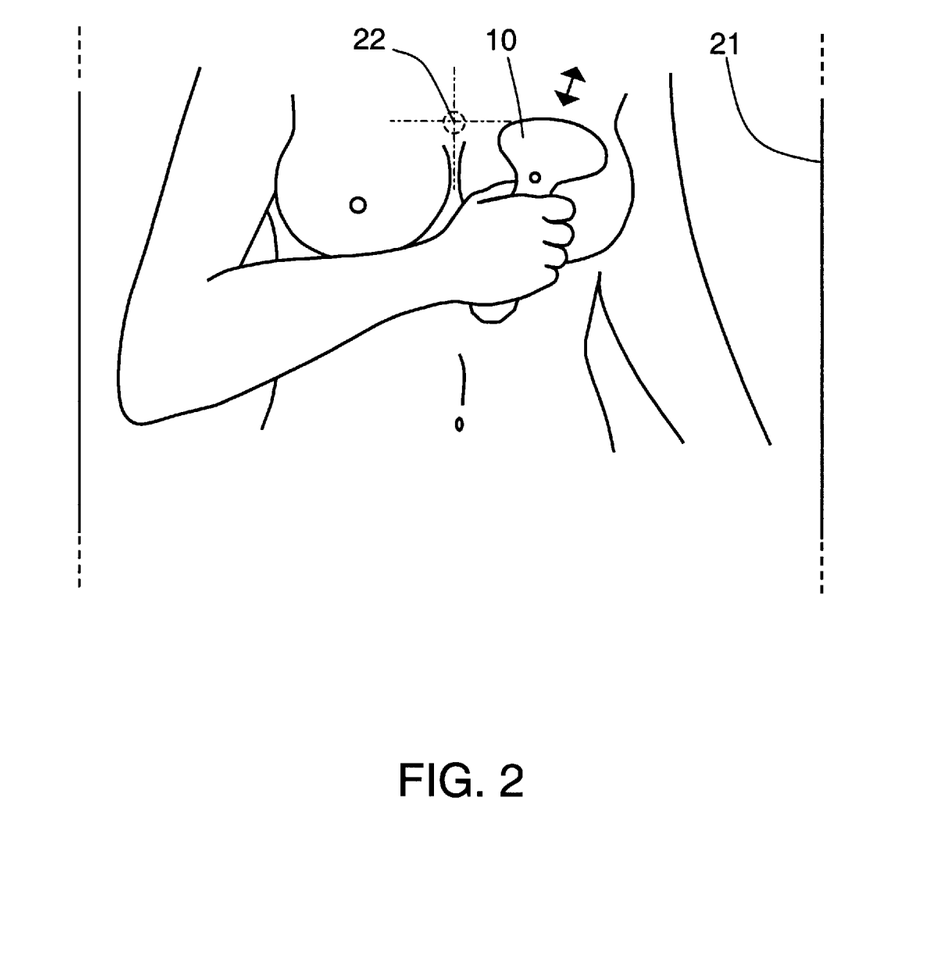
FIG. 2 is a schematic illustration of breast examination procedure using a hand held self-palpation device in accordance with the present invention showing a patient being self-examined.

During breast self-examination the patient can lie in a bed 21 or another suitable surface, as shown in FIG. 2. Such examination position allows the pectoral muscles to relax for greater access to the breast tissue providing reproducible breast examination data. The breast examination procedure includes a plurality of local scanning overlaying the breast. During breast examination, in accordance with the present invention, device 10 is moved from a reference point 22 above the breast surface to sites of breast to be scanned. Each scanning comprises the following steps: (1) pressing the pressure sensing surface 18 of device 10 against the breast tissue portion until a predetermined level of total pressure on pressure sensor array 11 is reached; (2) oscillating the pressure sensing surface over the breast tissue portion; (3) detecting pressure patterns from said pressure sensor array 11 and oscillatory signals from motion tracking system 12; (4) calculating position and orientation data from said oscillatory signals; and (5) processing the pressure patterns. Processed patterns are analyzed to reveal tissue abnormality and eliminate the signals from normal breast structures such as ribs, nipple, ligaments, and the like. The processed patterns are analyzed with decision support software. If this analysis performed by the decision support software unambiguously reveals tissue abnormality, electronic unit 13 generates a warning signal on display 15.

Figure 3A:
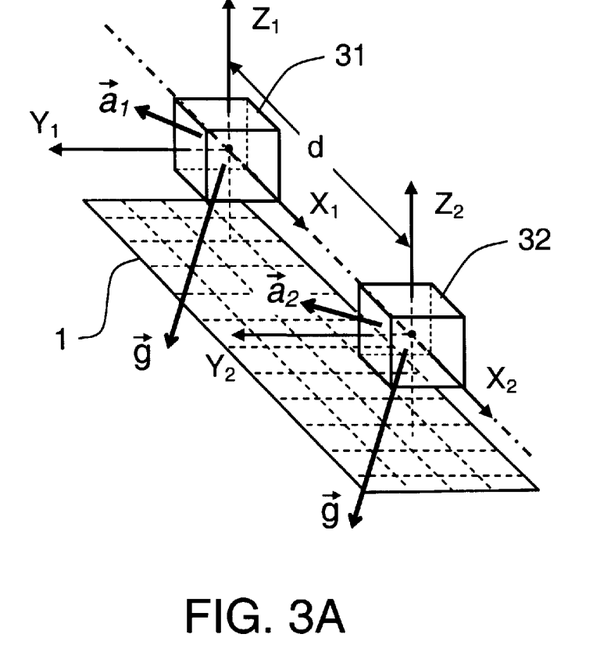
FIG. 3A is a schematic diagram of a motion tracking system including accelerometer sensors in accordance with an embodiment of the device of the present invention.

FIG. 3A is a schematic diagram of an accelerometer based motion tracking system which includes at least two three-axis accelerometers 31 and 32 separated by distance d and having sensitivity axes $X_1$, $Y_1$, $Z_1$ and $X_2$, $Y_2$, $Z_2$. For Example, the accelerometers can be, polysilicon surface micro-machined sensors. Preferably axes $X_1$, $X_2$ are coincident and the other axes are pairwise parallel. All sensors are fixed in a frame of reference of pressure sensor array 11. Each acceleration sensor provides a signal that is generally proportional to the acceleration along the corresponding axis. Under pressure sensor array 3-D motion during the breast examination, the acceleration vectors $a_1$ and $a_2$ are different except for rectilinear motion. This fact can be used for determination of linear and angular accelerations for the pressure sensor array. Accelerometer orientation relative to gravitational component (g-vector) can be evaluated considering accelerometer 31 as a tilt sensor at the reference point, such as the sternum, when both all velocities and all accelerations are zero (stationary point). Analysis of pressure response data at a reference point provides precise determination of the stationary point and provides the opportunity to exclude the gravitational component from acceleration signals. Double integration of acceleration signals provides the trajectory and orientation of pressure sensor array 11

Figure 3B:
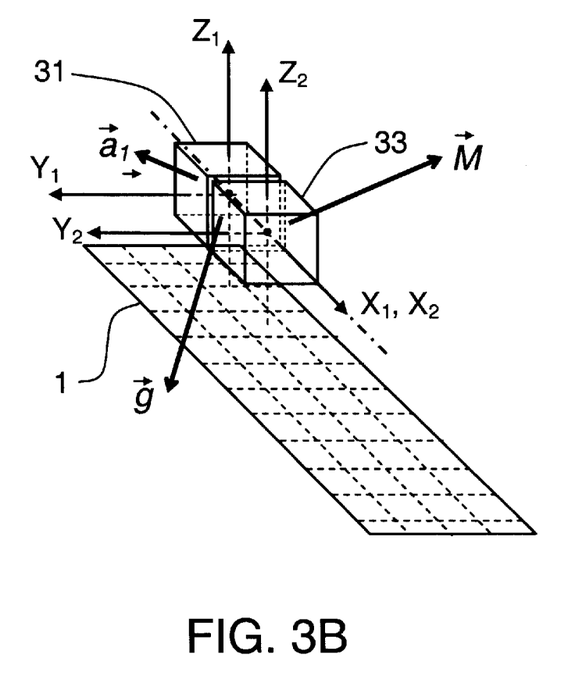
FIG. 3B is a schematic diagram of a motion tracking system including accelerometer sensors and magnetometer sensors in accordance with an embodiment of the device of the present invention.

FIG. 3B shows motion tracking system comprising at least one three-axis accelerometer 31 having sensitivity axes $X_1$, $Y_1$, $Z_1$ and one three-axis magnetometer 33 having sensitivity axes $X_2$, $Y_2$, $Z_2$. The magnetometer can be, for example, magnetoresistive micro-machined sensors. The sensors 31 and 33 are arranged in immediate proximity to each other so that axes $X_1$, $X_2$ are coincident and the other axes are pairwise parallel. All sensors are fixed in the frame of reference of pressure sensor array 11. Each acceleration sensor provides a signal that is generally proportional to the acceleration along the corresponding axis, and each magnetometer sensor provides a signal that is generally proportional to the Earth's magnetic field (M-vector) projection on the corresponding axis. The relative orientation of g-vector and M-vector can be connected using the stationary point. Such stationary point can be any point before the breast examination excluding magnetic materials in the immediate vicinity and provides the opportunity to exclude the gravitational component from acceleration signals. Double integration of acceleration signals provides the trajectory of pressure sensor array 11.

Figure 4:
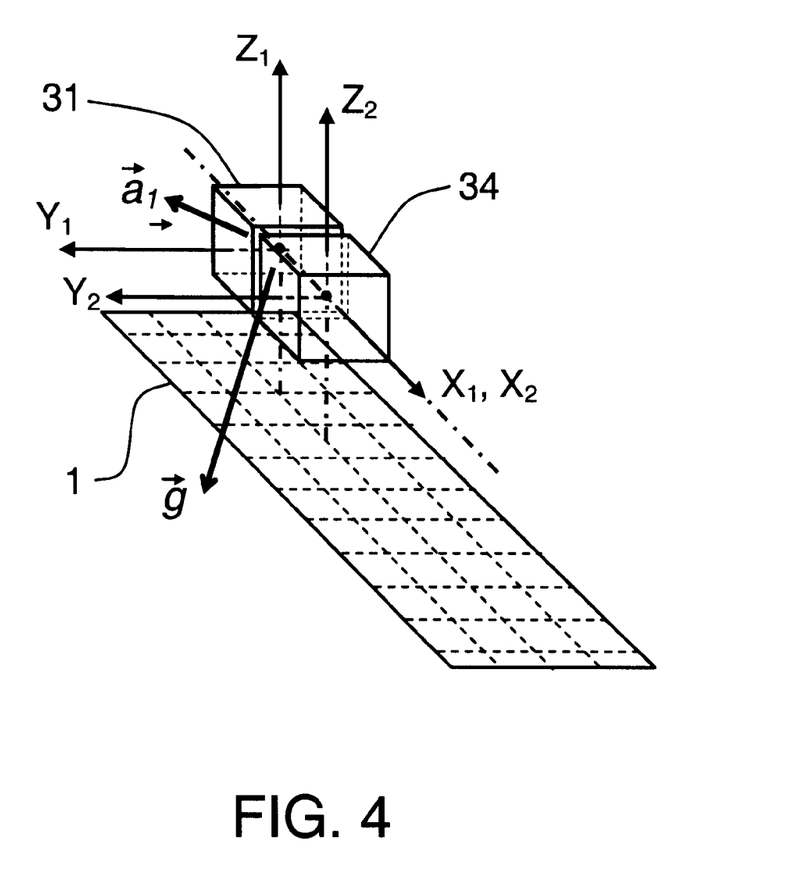
FIG. 4 is a schematic diagram of a motion tracking system including accelerometer sensors and gyroscopes in accordance with an embodiment of the device of the present invention.

Referring to FIG. 4, motion tracking system comprises at least three accelerometer sensors 31 having sensitivity axes $X_1$, $Y_1$, $Z_1$ and three angular rate sensors 34 having sensitivity axes $X_2$, $Y_2$, $Z_2$. The accelerometers can be, for example, micro-machined vibrating rotation sensors or small rotating gyroscopes. The sensors 31 and 34 are arranged in immediate proximity to each other so that axes $X_1$, $X_2$ are coincident and the other axes are pairwise parallel. All sensors are fixed in the frame of reference of pressure sensor array 11. Each acceleration sensor provides a signal that is generally proportional to the acceleration along the corresponding axis, and each angular rate sensor provides a signal that is generally proportional to the rate of rotation about the corresponding axis. Integrating angular rate signals provides orientation data relative to some reference orientation of pressure sensor array 11. It provides the opportunity to exclude the gravitational component from acceleration signals and then double integration of acceleration signals provides the trajectory of pressure sensor array 11.

A mechanism for obtaining accurate position and orientation data using the above-described motion tracking system is a correction process performed by a Kalman filter. The breast examination procedure includes multiple returns at a reference point and using the pressure response data to extract the device trajectory from the reference point to site of the breast to be scanned. During the breast scanning by an oscillatory manner the pressure response data is used to correct the trajectory and orientation of pressure sensing surface taking into account displacement of total pressure patterns on pressure sensor array, which characterize a linear motion of the device and changes in angle orientation.

Figure 5:
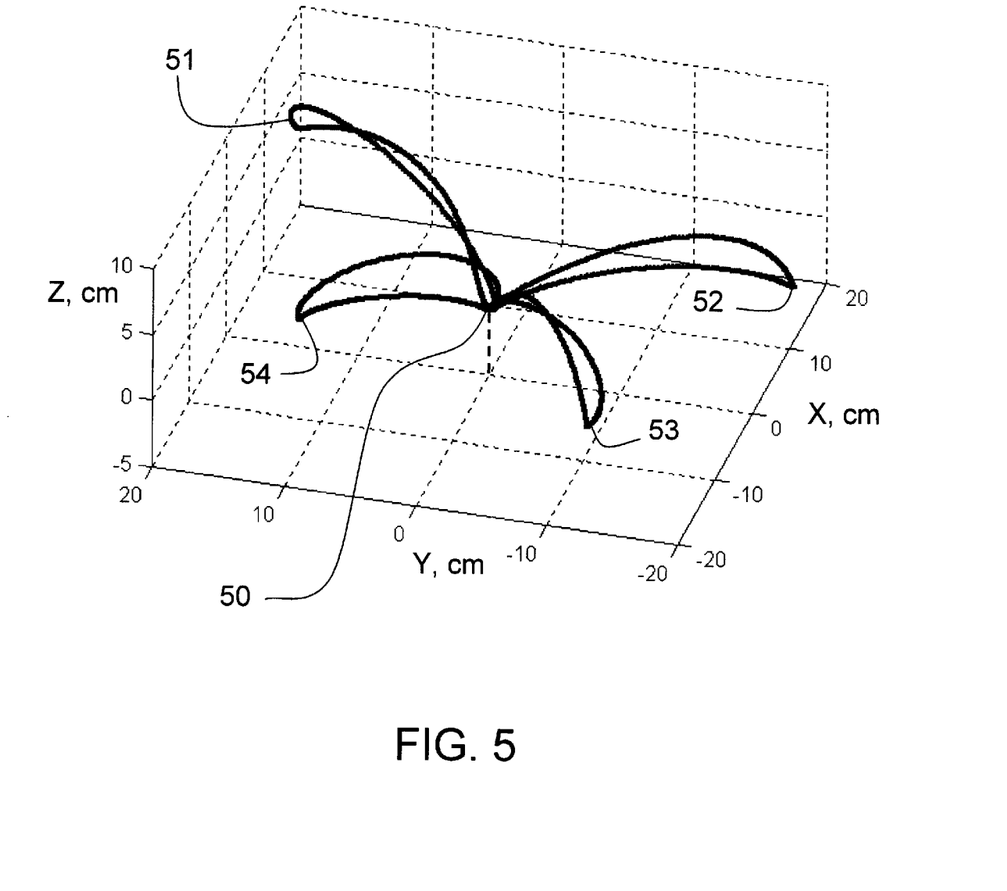
FIG. 5 is a calculated trajectory of the self-palpation device with an accelerometer based motion tracking system in a model experiment.

An example of the trajectory of the device in a model experiment calculated in accordance with the described above algorithm is shown in FIG. 5 using the accelerometer based motion tracking system of FIG. 3A. The pressure sensor array integrated with the motion tracking system has been moved from reference point 50 to points 51–54 each time returning at the same reference point 50.

Figure 6A:
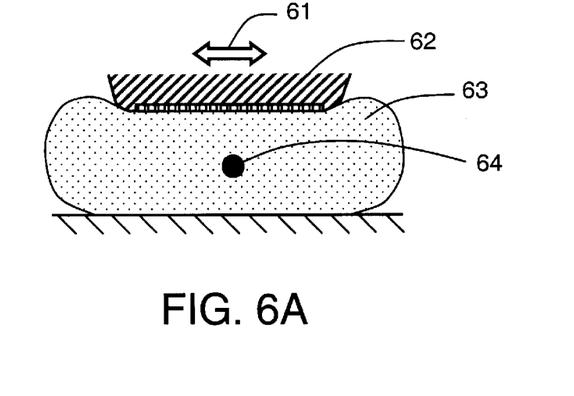
FIG. 6A shows the hand held self-palpation device with two-dimensional pressure sensor array in a model experiment with a breast phantom comprising a non-palpable nodule. Examination is performed in the oscillation mode.
Figure 6B:
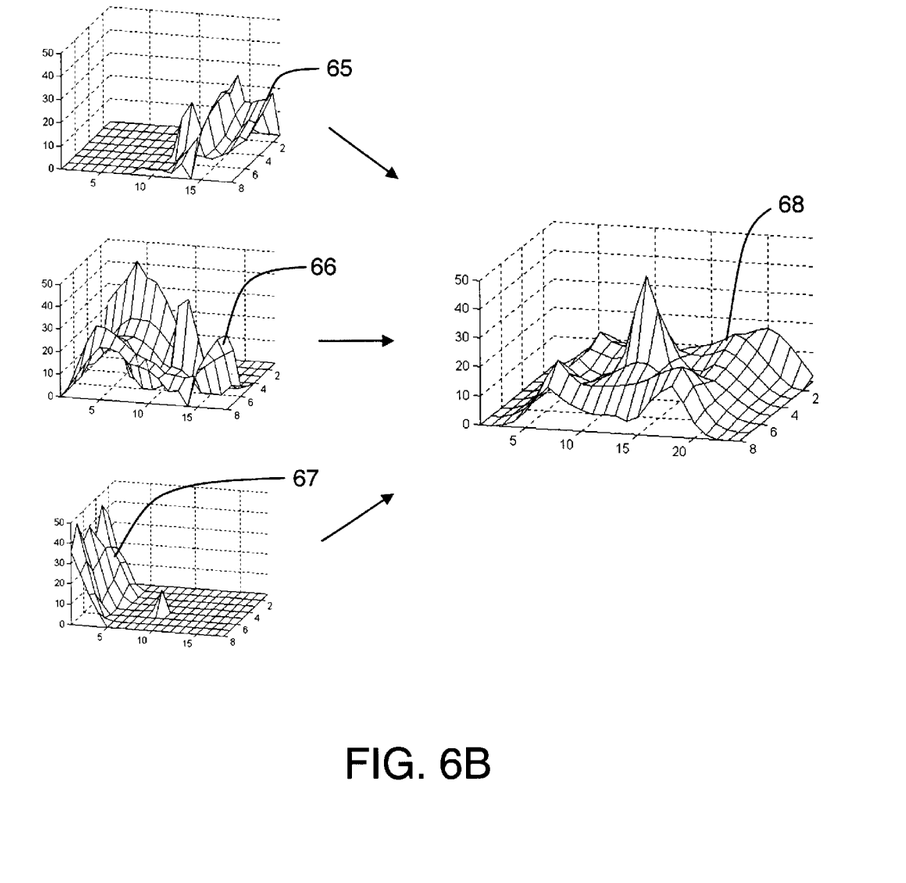
FIG. 6B is an illustration of one of the data analyzing algorithms in accordance with an embodiment of the method of the present invention.

FIG. 6A shows the hand held self-palpation device 10 with two-dimensional pressure sensor array 62 in a model experiment with a breast phantom 63 comprising a non-palpable nodule 64. Scanning was performed in a linear oscillation mode as shown by arrow 61 under pressing against phantom 63. FIG. 6B is an illustration of one of the data analyzing algorithms in accordance with an embodiment of the method of the present invention that dramatically increases the sensitivity of the device. The pressure patterns 65–67 on the left hand side represent a few single pressure patterns collected in the course of measurement. The plurality of all pressure patterns is summed up after spatially shifting every pattern by a pre-calculated value in an opposite direction of pressure sensor array motion. FIG. 68 shows the result of such analysis using the phantom data obtained in the experiment of FIG. 6A. This procedure allows multiple increasing signal-to-noise merit.

Figure 7:
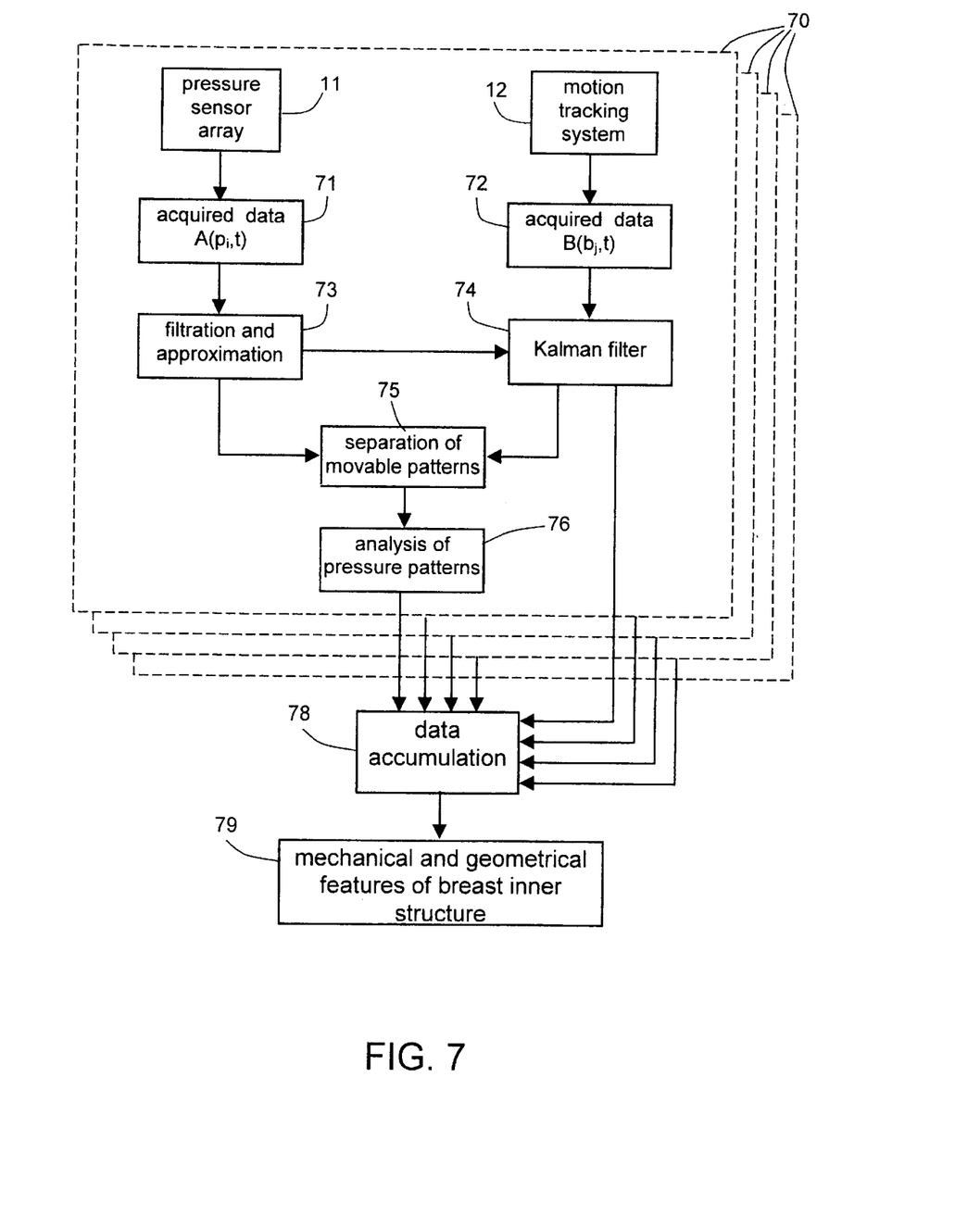
FIG. 7 is a flow chart describing steps for obtaining diagnostic information in accordance with an embodiment of the method of the present invention.

FIG. 7 is a flow chart describing steps for obtaining diagnostic information in accordance with an embodiment of the method of the present invention. Breast examination consists of a plurality of scans 70 overlying the breast. Pressure data from pressure sensor array 11 and position data from motion tracking system 12 are acquired in real time during breast examination. Analog signals corresponding to pressures received from all pressure transducers of pressure sensor array 11 form pressure data set 71 denoted by $A(p_i,t)$, where $p_i$ is pressure signal for pressure transducer with number i at time t. Analog signals representing accelerations and angular orientation of the device generated by motion tracking system 12 in response to movement of the device during breast examination, form motion data set 72 denoted as $B(b_j,t)$, where $b_j$ is signal corresponding to j motion sensor at time t. In block 73, pressure data set 71 is filtered by a band-pass filter and processed by a conventional approximation method, such as described for example by T. J. Rivlin, *An introduction to the Approximation of Functions*, Dover Publications, Inc., New York (1969), to reduce noise originating from pressure measurement errors and from skewing of pressure sensing surface during pressing against the breast. Further, motion data set 72 is processed by a suitable Kalman filter in block 74 to calculate the trajectory and orientation of the pressure sensing surface during breast scan correcting said trajectory and orientation using pressure response data from pressure sensor array 11 as it was described above. In block 75, pressure response data and motion data are processed by means of cumulative summation of a plurality of pressure patterns after spatially shifting every pattern by a pre-calculated value in an opposite direction of pressure sensor array motion to separate movable patterns in mechanical images, such as by using spatial and temporal deviations. Analysis of movable patterns enables detection of hard lesions in breast tissue on the background of signals from normal breast structures such as ribs, nipple, ligaments, etc. All operations in blocks 70 take place in real time during each breast scan.

Simultaneously, the breast examination data are accumulated in block 78, whereby the coordinates of each scan are calculated in the coordinate system with the origin at sternum 22 (see FIG. 2). After the breast examination is completed 3-D mechanical image of the breast including mechanical and geometrical features of breast inner structures are formed in block 79.

Figure 8:
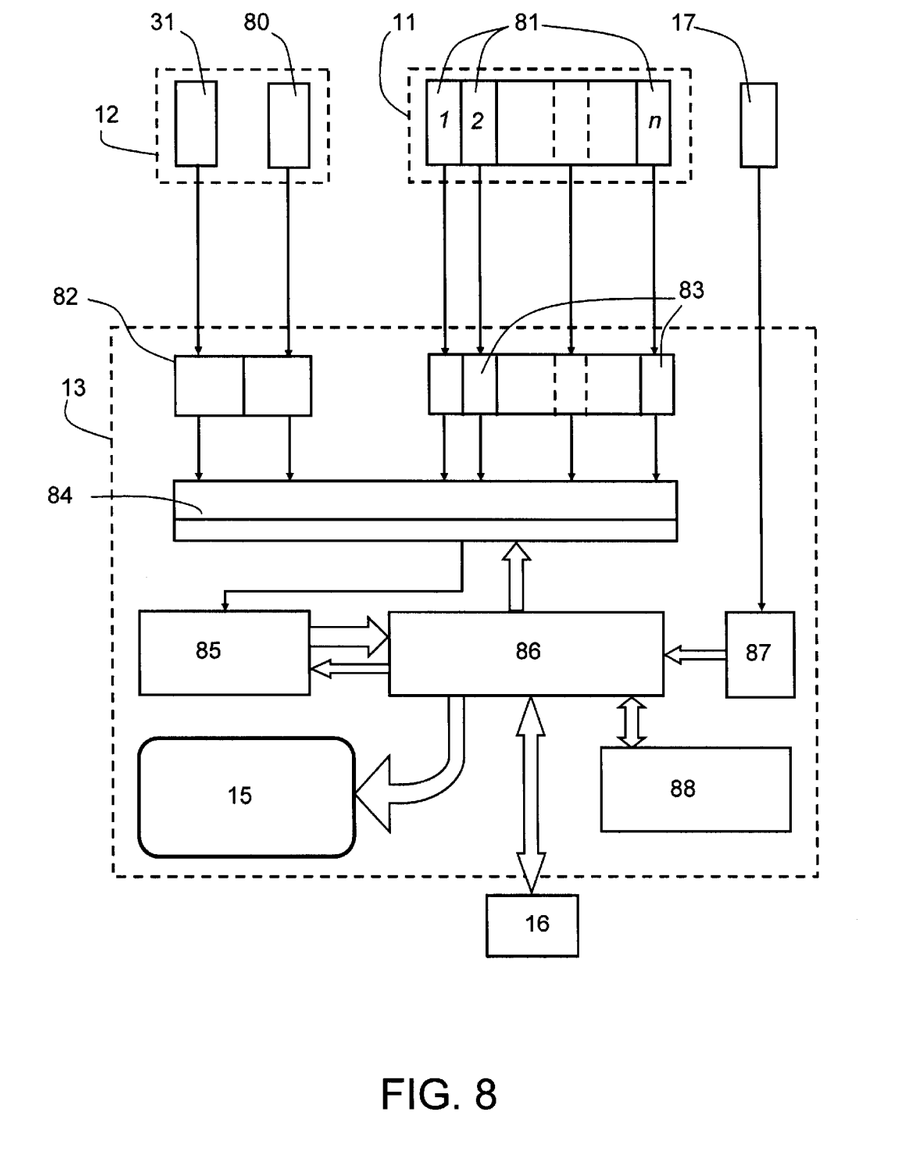
FIG. 8 is a schematic diagram illustrating the functional structure of the hand held self-palpation device in accordance with an embodiment of the device of the present invention.

FIG. 8 is a schematic diagram illustrating a preferred embodiment of electronic unit 13 incorporated in the device 10 shown in FIG. 1. Pressure sensing circuit 83 is formed of a plurality of amplifiers, converters and integrators to amplify and convert respective signals generated by pressure transducer elements 81 for detecting the pressure imposed on each pressure transducer element 81 of pressure sensor array sensor 11 during breast examination. A plurality of amplifiers 82 amplify signals generated by respective accelerometer 31 and magnetometer 32 of motion tracking system 12, for detecting the position and orientation of the pressure sensing surface during pressing against the breast tissue portion and movement of the device from one scan to another. The amplified signals from amplifiers 82 and 83 are applied to multiplexer 84. Multiplexed signals are converted to digital signals by analog-to-digital converter 85 and fed to processor 86. Processor 86 is used for signal processing to calculate the position of each of pressure transducer elements 81 during breast examination, to process the pressure patterns, for separation and analysis of the movable patterns in mechanical image, for determining the mechanical and geometrical features of breast inner structures such as lesions, nodules, stiffer tissue and the like.

Display 15 is connected to processor 86 to produce warning visual information during breast examination on the presence of foreign structures such as cysts, solid mass, and other lumps with respect to normal tissue stiffness. Information about the necessity to repeat scan in appropriate sites also could be shown on the display 15. Control wheel 17 is connected to processor 86 through controller 87 for controlling the device operation. Processor 86 communicates with analog-to-digital converter 85 and multiplexer 84 for sending data and control signals. Storage unit 88 can be used in electronic unit 13 for storing the results of the breast examination generated by processor 86 having computer port 16 to transfer the stored data to an external computer.

Although certain presently preferred embodiments of the present invention have been specifically described herein, it will be apparent to those skilled in the art to which the invention pertains that variations and modifications of the various embodiments shown and described herein may be made without departing from the spirit and scope of the invention.

What is claimed is:

1. A method of detecting changes in mechanical and structural properties of breast tissue that are indicative of breast cancer development, said method comprising the steps of:

scanning the breast tissue by means of a hand held self-palpation device having a pressure sensor array integrate with a self-contained motion tracking system;

acquiring pressure response data from said pressure sensor array and motion data from said motion tracking system during movement of said pressure sensor array along a plurality of trajectories overlaying said breast tissue;

calculating position an orientation data of said pressure sensor array from said motion data and said pressure response data;

analyzing said pressure response data and said motion data; and determining mechanical and geometrical features of an inner structure of the breast tissue from said analyze said pressure response data and said motion data.

2. The method of claim 1 wherein said scanning comprises the steps of:

pressing a pressure sensing surface of said device against a portion of said breast tissue until a predetermined level of total pressure on said pressure sensor array is reached, said pressure sensing surface coupled to said pressure sensor array; and oscillating said pressure sensing surface over said portion of breast tissue.

3. The method of claim 2 wherein said oscillating is performed by moving said pressure sensing surface in a circular manner in a plane of said pressure sensor array.

4. The method of claim 1 wherein said plurality of trajectories comprises trajectories originating at a reference point, moving to sites of the breast tissue, and ending at said reference point.

5. The method of claim 4 wherein said reference point is sternum.

6. The method of claim 4 wherein said analyzing of said motion data comprises calculation of a motion trajectory and an orientation of said pressure sensor array during breast examination in a coordinate system having an origin at said reference point.

7. The method of claim 1 wherein said calculating position and orientation data comprises correction of said position data taking into account the displacement of said pressure sensor array calculated from temporal and spatial derivatives of pressure patterns.

8. The method of claim 7 wherein said calculating position and orientation data comprise correction of said orientation data taking into account a change of angle orientation of said pressure sensor array.

9. The method of claim 1 wherein said determining mechanical and geometrical features of the breast inner structures is based on separation of movable patterns in mechanical images.

10. The method of claim 1 wherein said determining mechanical and geometrical features of the breast inner structures includes formation of a three dimensional mechanical image of the breast by combining results of said scanning of the breast tissue at all sites of the breast.

11. A method of detecting changes in mechanical and structural properties of breast tissue that are indicative of breast cancer development, said method comprising the steps of:
   scanning the breast tissue by means of a hand held self-palpation device having a pressure sensor array integrate with a self-contained motion tracking system;
   acquiring pressure response data from said pressure sensor array and motion data from said motion tracking system during movement of said pressure sensor array along a plurality of trajectories overlaying said breast tissue;
   calculating position an orientation data of said pressure sensor array from said motion data and said pressure response data;
   analyzing said pressure response data and said motion data;
   determining mechanical and geometrical features of an inner structure of the breast tissue from said analyzed said pressure response data and said motion data; and
   analyzing said motion data comprises calculation of a motion trajectory and an orientation of said pressure sensor array during breast examination in a coordinate system having an origin at a reference point,
   wherein said calculation of said motion trajectory and said orientation comprises correcting said motion trajectory and said orientation with a Kalman filter using said pressure response data from said pressure sensor array.

12. A method of detecting changes in mechanical and structural properties of breast tissue that are indicative of breast cancer development, said method comprising the steps of:
   scanning the breast tissue by means of a hand held self-palpation device having a pressure sensor array integrated with a self-contained motion tracking system;
   acquiring pressure response data from said pressure sensor array and motion data from said motion tracking system during movement of said pressure sensor array along a plurality of trajectories overlaying said breast tissue;
   calculating position and orientation data of said pressure sensor array from said motion data and said pressure response data;
   analyzing said pressure response data and said motion data; and
   determining mechanical and geometrical features of an inner structure of the breast tissue from said analyzed said pressure response data and said motion data,
   wherein said analyzing comprises cumulative summation of a plurality of pressure patterns after spatially shifting every pattern by a precalculated value in opposite direction of motion at said pressure sensor array.

13. A hand held device for detecting changes in mechanical and structural properties of breast tissue that are indicative of breast cancer development, said device comprising:
   a pressure sensor array having a plurality of pressure sensors, each of said sensors producing a signal in response to pressure imposed on the sensor as the sensors are pressed and moved against the breast tissue in a predetermined manner;
   a self-contained motion tracking system integrated with said pressure sensor array;
   an electronic unit for providing acquisition of said signals from said pressure sensor array and signals from said motion tracking system, processing said signals as data pressure response data and motion data, real time displaying of said pressure response data and said motion data and storing of said pressure response data and said motion data,
   wherein said motion tracking system comprises at least two three-axis accelerometers separated by a distance from one another.

14. A hand held device for detecting changes in mechanical and structural properties of breast tissue that are indicative of breast cancer development, said device comprising:
   a pressure sensor array having a plurality of pressure sensors, each of said sensors producing a signal in response to pressure imposed on the sensor as the sensors are pressed and moved against the breast tissue in a predetermined manner;
   a self-contained motion tracking system integrated with said pressure sensor array;
   an electronic unit for providing acquisition of said signals from said pressure sensor array and signals from said motion tracking system, processing said signals as data pressure response data and motion data, real time displaying of said pressure response data and said motion data and storing of said pressure response data and said motion data,
   wherein said motion tracking system comprises at least one three-axis accelerometer and three-axis magnetometer and wherein accelerometer sensitivity axes are parallel to magnetometer sensitivity axes.

15. A hand held device for detecting changes in mechanical and structural properties of breast tissue that are indicative of breast cancer development, said device comprising:
   a pressure sensor array having a plurality of pressure sensors, each of said sensors producing a signal in response to pressure imposed on the sensor as the sensors are pressed and moved against the breast tissue in a predetermined manner;
   a self-contained motion tracking system integrated with said pressure sensor array;
   an electronic unit for providing acquisition of said signals from said pressure sensor array and signals from said motion tracking system, processing said signals as data pressure response data and motion data, real time displaying of said pressure response data and said motion data and storing of said pressure response data and said motion data, wherein said motion tracking system comprises a three-axis accelerometer and three-axis magnetometer, wherein accelerometer sensitivity axes are parallel to magnetometer sensitivity axes and two said accelerometer sensitivity axes are parallel to a sensing surface of said pressure sensor array.

16. A hand held device for detecting changes in mechanical and structural properties of breast tissue that are indicative of breast cancer development, said device comprising:

a pressure sensor array having a plurality of pressure sensors, each of said sensors producing a signal in response to pressure imposed on the sensor as the sensors are pressed and moved against the breast tissue in a predetermined manner;

a self-contained motion tracking system integrated with said pressure sensor array;

an electronic unit for providing acquisition of said signals from said pressure sensor array and signals from said motion tracking system, processing said signals as data pressure response data and motion data, real time displaying of said pressure response data and said motion data and storing of said pressure response data and said motion data, wherein said motion tracking system comprises at least one three-axis accelerometer and three-axis gyroscope and wherein accelerometer sensitivity axes are parallel to gyroscope sensitivity axes.

17. A hand held device for detecting changes in mechanical and structural properties of breast tissue that are indicative of breast cancer development, said device comprising:

a pressure sensor array having a plurality of pressure sensors, each of said sensors producing a signal in response to pressure imposed on the sensor as the sensors are pressed and moved against the breast tissue in a predetermined manner;

a self-contained motion tracking system integrated with said pressure sensor array;

an electronic unit for providing acquisition of said signals from said pressure sensor array and signals from said motion tracking system, processing said signals as data pressure response data and motion data, real time displaying of said pressure response data and said motion data and storing of said pressure response data and said motion data, wherein said electronic unit comprises:

a pressure sensing circuit including a plurality of amplifiers to amplify respective signals generated by said pressure sensor array;

a plurality of multiplexers to multiplex electrical signals from said amplifiers; an analog-to-digital converter;

a processor to synchronize and filtrate said pressure response data received from said pressure sensors and said motion data received from said motion tracking system, to analyze said pressure response data and said motion data and to determine the mechanical and geometrical features of underlying breast tissue;

a display connected to said processor to monitor examination of said breast tissue to provide feedback and to represent the results of the examination;

a control unit connected to said processor to control an operation mode of said device; and a communication port to transfer said pressure response data and said motion data into an external computer.

* * * * *